United States Patent [19]

Kleiner

[11] 4,069,247
[45] Jan. 17, 1978

[54] PREPARATION OF PHOSPHONIC AND/OR PHOSPHINIC ACIDS

[75] Inventor: Hans-Jerg Kleiner, Kronberg, Taunus, Germany

[73] Assignee: Hoechst Aktiengesellschaft, Frankfurt am Main, Germany

[21] Appl. No.: 609,080

[22] Filed: Aug. 29, 1975

[30] Foreign Application Priority Data

Aug. 31, 1974 Germany .............................. 2441783

[51] Int. Cl.$^2$ ........................ C07F 9/30; C07F 9/38; C07C 27/00
[52] U.S. Cl. ...................... 260/502.4 R; 260/502.4 P; 260/632 R; 260/633
[58] Field of Search .................. 260/502.4 R, 502.4 P, 260/632 R, 633

[56] References Cited

U.S. PATENT DOCUMENTS 2,776,985    1/1957    McKinnis .................... 260/502.4 R
3,666,838    5/1972    Kollonitsch et al. ......... 260/502.4 R

OTHER PUBLICATIONS

Lange, "Handbook of Chemistry", 10th ed. (1961), pp. 642 and 643.
Horsley, "Azeotropic D.J.-III", 1973, pp. 15, 18, 38, 460, 461.
Canavan et al., "J. Chem. Soc." (London) Jan. 1962, pp. 331-334.

*Primary Examiner*—Joseph E. Evans
*Attorney, Agent, or Firm*—Curtis, Morris & Safford

[57] ABSTRACT

Preparation of phosphonic and/or phosphinic acids by hydrolytic cleavage of phosphonic and/or phosphinic acid alkyl esters in the presence of the phosphonic and/or phosphinic acid by carrying out the hydrolysis at a temperature of from 170° to 300° C with the use of at least a stoichiometric amount of water, and by distilling off the alkanol formed, optionally together with water.

13 Claims, No Drawings

PREPARATION OF PHOSPHONIC AND/OR PHOSPHINIC ACIDS

The present invention relates to a process for the preparation of phosphonic and phosphinic acids.

The processes hitherto known for the preparation of phosphonic or phosphinic acids from the corresponding alkyl esters easily obtainable are generally carried out using mineral acids or hydrogen halides. They have many disadvantages; thus, they require special methods for the purification of the final product to liberate it from the mineral acids used, or they cause the formation of considerable amounts of by-products.

Another process is known according to which phosphonic or phosphinic acid alkyl esters, in the presence of the corresponding phosphonic or phosphinic acids, are subjected to a hydrolytic splitting at temperatures of from 90° to 150° C. The reaction temperatures are expressly limited to a maximum of 150° C, preferably 140° C, since only up to these temperatures decomposition and discoloration of the products are avoided. However, this process so far has not been applied on an industrial scale since the necessary reaction times are too long.

Surprisingly, there has now been found a process for the preparation of phosphonic and/or phosphinic acids by saponification of the corresponding phosphonic and/or phosphinic acid alkyl esters, which process overcomes the disadvantages of the known processes and gives phosphonic and/or phosphinic acids of excellent quality with practically quantitative yields.

Subject of the present invention is therefore a process for the preparation of phosphonic and/or phosphinic acids of the formula (I)

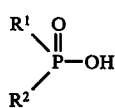

(I)

were $R^1$ is an alkyl radical having from 1 to 20 carbon atoms, an alkenyl radical having from 2 to 20 carbon atoms, an aralkyl radical having from 7 to 12 carbon atoms or an aryl radical having from 6 to 10 carbon atoms, these radicals optionally being mono- to trisubstituted, preferably monosubstituted, by Cl, Br, alkyl or alkoxy groups each having from 1 to 4 carbon atoms; or $R^1$ is a radical of the formula (Ia)

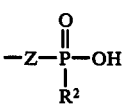

(Ia)

where Z is an alkylene radical having from 2 to 6 carbon atoms, a phenylene, biphenylene, naphthylene radical or a radical or the formula (Ib)

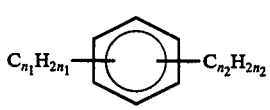

(Ib)

wherein $n_1$ and $n_2$ are identical or different integers of from 1 to 4, preferably $n_1 = n_2 = 1$; and $R^2$ in the formulae (I) and (Ia) is either as defined for $R^1$, except the radical of formula (Ia), $R^1$ and $R^2$ being either identical or different, or OH; by hydrolytic cleavage of phosphonic and/or phosphinic acid alkyl esters of the formula (II)

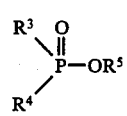

(II)

wherein $R^3$ is as defined above for $R^1$ except the radical of formula (Ia), or a radical of the formula (IIa)

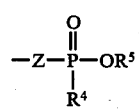

(IIa)

where Z is as defined in formula (Ia), and $R^4$ in formulae (II) and (IIa) is either as defined for $R^3$ except the radical of formula (IIa), $R^3$ and $R^4$ being either identical or different, or $OR^5$ or OH, $R^5$ being a straight-chain or branched alkyl group having from 2 to 8, preferably from 2 to 4 carbon atoms, optionally being substituted, preferably monosubstituted, by chlorine or bromine; in the presence of the phosphonic and/or phosphinic acid of formula (I), which comprises carrying out the hydrolysis at a temperature of from 170° to 300° C, preferably from 190° to 230° C, with the use of at least a stoichiometric amount of water, and by distilling off the alkanol formed, optionally together with water.

The process of the invention is generally carried out as follows: the ester of formula (II) and from 2 to 30 weight %, preferably from 5 to 20 weight %, relative to the ester, of the corresponding acid of formula (I) are heated to the desired reaction temperature, and then the water is added in such a manner that the reaction temperature is maintained. Also alkanol containing water may be used for the hydrolysis. A good intermixing of the reactants is recommended.

Of course, the reaction mixture and the water may be heated simultaneously to reaction temperature with water optionally distilling off, and the water still required after having attained the reaction temperature may be added as indicated above. It is also possible to heat the ester of formula (II) alone to reaction temperature and to add subsequently a solution of the desired amount of acid of formula (I) in the required amount of water. The upper limit of the acid/ester ratio is set only by economic considerations; anyhow it rises towards infinity with the hydrolysis proceeding.

According to the process of the invention, the alkanol formed in the reaction is distilled off, preferably in usual manner via a distillation column or an equivalent device, optionally in the form of an azeotropic mixture; entrained water which possibly separates in the condensation of the azeotropic mixture being eliminated and recycled into the hydrolysis.

As stoichiometric amount, there is required 1 mol of water for each ester group of the compound of formula (II). Generally, however, it is advantageous to use an excess of water, which depends above all of the efficiency of the device used for separating the alkanol and on the amount of water entrained by the azeotropic mixture. On the average, in the case of industrial equipment, a water excess of from 50 to 200% above the stoichiometric amount is used. In order to accelerate the hydrolysis and to complete it more rapidly, it may be advantageous to add large amounts of water towards the end of the hydrolysis, so that the excess may amount to 200% and more. The alkanol containing water obtained may be reused for a further hydrolysis. Water excesses of more than 200%, for example up to 300% or more may be used without adversely affecting the process, but they are disadvantageous because the alkanol contained in the excess water, for reasons of preventing pollution, would have to be eliminated by distillation. The pressure to be chosen for the process of the invention is not critical, but the process is preferably carried out under atmospheric pressure. However, any other pressure, especially elevated pressure, may also be applied, preferably a pressure below the vapor pressure of the water and/or the alkanol at reaction temperature.

By adding a quantity of water below the stoichiometric amount, it is possible to attain a partial hydrolysis only, so that mixtures of esters, semi-esters and/or acids are obtained.

The process may be carried out batchwise or continuously.

The reaction temperatures are from 170° to 300° C, preferably from 190° to 230° C; the reaction temperatures required rising towards the upper limit of the intervals with increasing number of carbon atoms in the radicals $R^1$ to $R^5$.

Of course, the hydrolysis of the esters of formula (II) according to the process of the invention may be carried out also in the presence of other acidic catalysts, for example sulfuric or p-toluenesulfonic acid. Thus, the hydrolysis of an ester of formula (II) may be started also in the absence of an acid of formula (I), by adding first small amounts, that is, preferably from 2 to 10 mol %, relative to the ester of formula (II), of aqueous or gaseous HCl at reaction temperature, so that the amount of phosphonic or phosphinic acid desired for continuing the hydrolysis is produced in situ. However, the formation of the corresponding alkane chloride must be taken into consideration in this case. When the methyl esters of formula (II) are used, the hydrolysis starts at reaction temperature by adding water alone. However, an especially advantageous embodiment of the process of the invention is based on avoiding the use of catalysts foreign to the system, thus allowing the obtension of the desired final products in pure form and practically free from water. Contrary to the teaching of the state of the art, at the elevated temperatures of the process of the invention at which the reaction mixture cannot but dissolve small amounts of water, the hydrolysis proceeds not only with considerably increased reaction speed, but also decomposition and discoloration as described in the literature are not observed.

This result is very surprising, especially in the case of high molecular weight products. It is also surprising that at the reaction temperatures according to the invention practically no pyrophosphonic acids or anhydrides are formed and also dialkyl ethers or alkenes are formed to an insignificant extent only or not at all.

At starting products of formula (II), phosphonic acid dialkyl or monoalkyl esters, phosphinic acid alkyl esters and biphosphonic and biphosphinic acid alkyl esters are used, such as the diethyl, dipropyl, di-n-butyl, diisobutyl, dioctyl ester of ethanephosphonic acid, the diisobutyl esters of propanephosphonic acid and octanephosphonic acid, hexanephosphonic acid diisopropyl ester, octanephosphonic di-(2-ethylhexyl) ester, hexadecanephosphonic acid diethyl ester, chloromethanephosphonic acid isobutyl ester, p-bromobenzenephosphonic acid diethyl ester, octanephosphonic acid isobutyl ester, methylethylphosphinic acid ethyl ester and -isobutyl ester, methyloctylphosphinic acid isobutyl ester and -(2-ethylhexyl) ester, the isobutyl esters of methylvinylphosphinic acid, ethane-1,2-bis-methylphosphinic acid and phenylene-1,4-bismethylphosphinic acid, benzylphosphonic acid diethyl ester, the isobutyl esters of methylbenzylphosphinic acid and methylphenylphosphinic acid.

Mixtures of the corresponding mono- and dialkyl esters may also be used.

Preferred radicals $R^1$ or $R^2$ which according to formula (I) are linked to the phosphorus via a direct C — P bond are those containing from 1 to 16, especially from 4 to 12 carbon atoms.

It is recommended to carry out the hydrolysis, especially at the beginning of the reaction, in an inert gas atmosphere. As inert gases, there may be used for example nitrogen or argon or $CO_2$. The reaction may also be carried out in the presence of a high-boiling inert solvent such as o-di-chlorobenzene, dichlorotoluene, mono- or dichloroxylene.

After complete reaction, the phosphonic and phosphinic acids obtained as crude products may be purified according to known methods; phosphonic acids may for example be recrystallized, phosphinic acids distilled.

Phosphonic and phosphinic acids are interesting intermediate products, for example for the preparation of plant protection products. Furthermore, they may be used, optionally also in the form of their salts, as textile auxiliaries, antistatic or flame retarding agents, solutes, anti-corrosion or flotation auxiliaries.

The following examples illustrate the invention.

EXAMPLE 1

125 g of butanephosphonic acid di-n-butyl ester and 35 g of butanephosphonic acid are heated to 200° C. Subsequently, with vigorous agitation, a total of 60 ml of water is added dropwise within 4.5 hours. The n-butanol and excess water are distilled off via a distillation column. In a subsequent cooling trap, 3 g of butylene are collected, which corresponds to about 5.5 mol %, relative to the butanol amount theoretically obtained in the hydrolysis. The oily residue is 104 g of n-butanephosphonic acid, corresponding to a 100% yield.

EXAMPLE 2

300 g of methyloctylphosphinic acid isobutyl ester and 30 g of methyloctylphosphinic acid are heated to 200° —220° C. Subsequently, with vigorous agitation, 40 ml of water are added dropwise within 10 hours. The isobutanol and water are distilled off via a distillation column. In the distillate, isobutanol containing water separates as lower phase and is recycled into the reaction process. In a cooling trap, 2 g of isobutylene are collected, which corresponds to about 3 mol %, relative to the isobutanol amount theoretically obtained in the hydrolysis. The residue solidifies. 262 g of methyloctylphosphinic acid, solidifaction point 42.5° C, are obtained, corresponding to a yield of 100%.

EXAMPLE 3

1015 g of methylethylphosphonic acid isobutyl ester are combined with 10 ml of concentrated hydrochloric acid, and with vigorous nitrogen flushing, the mixture is heated to 190°–200° C. At this temperature, the flushing is stopped. Subsequently, with vigorous agitation, a total of 250 ml of water is added dropwise within 12 hours. Isobutanol and water are distilled off via a distillation column. In the distillate isobutanol containing water separates as lower phase and is recycled into the reaction process. In a cooling trap, 15 g of isobutylene are collected, corresponding to about 4.5 mol %, relative to the isobtanol amount theoretically obtained in the hydrolysis. The residue is 668 g of methylethylphosphinic acid, boiling point at 0.7 mm Hg 130°–132° C, which corresponds to a yield of 100%.

EXAMPLE 4

300 g of octanephosphonic acid diethyl ester and 30 g of octanephosphonic acid are heated to 190°–200° C. Subsequently, with vigorous agitation, 160 ml of water are added dropwise within 5 hours. 158 g of water containing ethanol (water content 34.3%) are distilled off via a distillation column, corresponding to a yield of 95% of ethanol. The residue solidifies. 263 g of octanephosphonic acid, solidification point about 85° C, are obtained, corresponding to yield of 100%.

EXAMPLE 5

600 g of octanephosphonic acid di-isobutyl ester and 60 g of octanephosphonic acid are heated to 195°–200° C with nitrogen flushing, which is stopped at this temperature. Subsequently, with vigorous agitation, 260 ml of water are added dropwise within 5 hours. Isobutanol and water are distilled off via a distillation column. In a subsequent cooling trap, 41 g of isobutylene are collected, which corresponds to about 18.5 mol %, relative to the isobutanol amount theoretically obtained in the hydrolysis. The residue solidifes. 440 g of octanephosphonic acid, solidification point about 85° C, are obtained, corresponding to a 100% yield.

I claim:
1. A process for the preparation of alkyl alcohols and phosphonic and/or phosphinic acids of the formula (I)

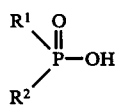
(I)

where R$^1$ is an alkyl radical having from 1 to 20 carbon atoms, an alkenyl radical having from 2 to 20 carbon atoms, an aralkyl radical having from 7 to 12 carbon atoms or an aryl radical having from 6 to 10 carbon atoms, these radicals optionally being mono- to trisubstituted by Cl, Br, alkyl or alkoxy groups each having from 1 to 4 carbon atoms; or R$^1$ is a radical of the formula (Ia)

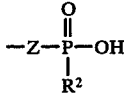
(Ia)

where Z is an alkylene radical having from 2 to 6 carbon atoms, a phenylene, biphenylene, naphthylene radical or a radical of the formula (Ib)

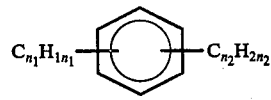
(Ib)

wherein $n_1$ and $n_2$ are identical or different integers of from 1 to 4, and R$^2$ in the formulae (I) and (Ia) is either as defined for R$^2$, except the radical of formula (Ia), R$^1$ and R$^2$ being either identical or different, or OH; by hydrolytic cleavage of phosphonic and/or phosphinic acid alkyl esters of the formula (II)

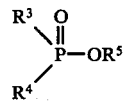
(II)

where R$^3$ is as defined above for R$^1$ except the radical of formula (Ia), or a radical of the formula (IIa)

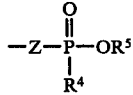
(IIa)

where Z is as defined in formula (Ia), and R$^4$ in formulae (II) and (IIa) is either as defined for R$^3$ except the radical of formula (IIa), R$^3$ and R$^4$ being either identical or different, or OR$^5$ or CH, R$^5$ being a straight-chain or branched alkyl group having from 2 to 8 carbon atoms, optionally being substituted by chlorine or bromine; in the presence of the phosphonic and/or phosphinic acid of formula (I), which comprises carrying out the hydrolysis at atmospheric pressure and at a temperature of from 170° to 300° C, with the use of at least a stoichiometric amount of water, and by distilling off the alcohol formed, optionally with water.

2. The process as claimed in claim 1, which comprises using the ester of formula (II) together with 2 to 30 weight % of the corresponding acid of formula (I), relative to the ester of formulae (II).

3. The process as claimed in claim 1, which comprises carrying out the reaction under an inert gas atmosphere.

4. The process as claimed in claim 1, which comprises hydrolytically producing at first the phosphonic or phosphinic acid of formula (I) required as catalyst in situ at reaction temperature by adding from 2 to 10 mol % of aqueous or gaseous HCl, relative to the ester of formula (II), distilling off the alkyl chloride possibly formed optionally with water and/or the alkanol, and continuing the hydrolysis according to the invention.

5. A process for the preparation of a straight chain or branch alkyl alcohol having 2 to 8 carbon atoms and a phosphonic acid of the formula III

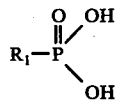
III wherein R$_1$ is a member selected from the group consisting of ethyl, propyl, hexyl, octyl, hexadecane, chloromethyl, benzyl and p-bromobenzene, or phosphinic acids of the formula V

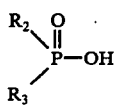

V wherein $R_2$ is methyl and $R_3$ is a member selected from the group consisting of ethyl, vinyl, octyl, phenyl and benzyl by a hydrolytic cleavage reaction of a phosphonic acid alkyl ester of the formula IV

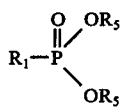

IV wherein $R_1$ is as defined above and each of $R_5$ is a member selected from the group consisting of ethyl, propyl, n-butyl, iso-butyl, 2-ethylhexyl, octyl, or one of said —$OR_5$ is a —OH or by a hydrolytic cleavage reaction of a phosphinic acid alkyl ester of the formula

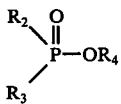

VI wherein $R_2$ and $R_3$ are as defined above and $R_4$ is a member selected from the group consisting of ethyl, isobutyl and 2-ethyl hexyl; wherein the hydrolytic cleavage reaction is carried out in the presence of 2 to 30 weight % of the respective phosphonic or phosphinic acid of formula III or V, based on weight of the corresponding phosphonic or phosphinic acid ester of formula IV or VI, respectively, to form the corresponding phosphonic acid and an alcohol or phosphinic acid and an alcohol, said reaction being carried out with at least a stoichiometric amount of water being present during the reaction or being gradually added during the reaction, and said reaction being carried out at atmospheric pressure and at a temperature of 170° to 300° C, distilling off the alcohol during the reaction, or distilling the alcohol and water during the reaction.

6. The process of claim 1 wherein the phosphonic acid is butane phosphonic acid and the phosphonic acid ester is butane phosphonic acid di-n-butyl ester.

7. The process of claim 1 wherein the phosphinic acid is methyl, octyl phosphinic acid and the phosphinic acid ester is methyl, octyl phosphinic acid iso-butyl ester.

8. The process of claim 1 wherein the phosphinic acid is methyl, ethyl phosphinic acid and the phosphinic acid ester is methyl, ethyl phosphinic acid iso-butyl ester.

9. The process of claim 1 wherein the phosphonic acid is octane phosphonic acid and the phosphonic acid ester is octane phosphonic acid diethyl ester.

10. The process of claim 1 wherein the phosphonic acid is octane phosphonic acid and the phosphonic acid ester is octane phosphonic acid di-isobutyl ester.

11. The process of claim 1 wherein the phosphinic acid is a member selected from the group consisting of ethane-1,2-bis-methylphosphinic acid and phenylene-1,4-bis-methylphosphinic acid and the phosphinic acid ester is a member selected from the group consisting of ethane-1, 2-bis-methylphosphinic acid isobutyl ester and phenylene-1,4-bis-methylphosphinic acid isobutyl ester.

12. A process for the preparation of a straight chain or branched chain alkyl alcohol having 2 to 8 carbon atoms and a phosphonic acid of the formula III

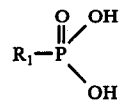

III wherein $R_1$ is a member selected from the group consisting of ethyl, propyl, hexyl, octyl, hexadecane, chloromethyl, benzyl and p-bromobenzene, by a hydrolytic cleavage reaction of a phosphonic acid alkyl ester of the formula IV

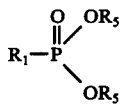

IV wherein $R_1$ is as defined above and each of $R_5$ is a member selected from the group consisting of ethyl, propyl, n-butyl, iso-butyl, 2-ethylhexyl, octyl, or one of said –$OR_5$ is a –OH, wherein the hydrolytic cleavage reaction is carried out in the presence of 2 to 30 weight percent of the phosphonic acid of formula III, based on weight of the corresponding phosphonic acid ester of formula IV, to form the corresponding phosphonic acid and an alkyl alcohol, said process consisting essentially of carrying out the reaction at atmospheric pressure and a temperature of about 170° to 300° C, while gradually adding during the reaction at least a stoichiometric amount of water sufficient to form said alkyl alcohol and distilling off the alkyl alcohol formed during the reaction.

13. A process for the preparation of a straight chain or branched chain alkyl alcohol having 2 to 8 carbon atoms and a phosphinic acid of the formula V

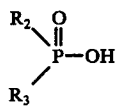

V wherein $R_2$ is methyl and $R_3$ is a member selected from the group consisting of ethyl, vinyl, octyl, phenyl and benzyl, by a hydrolytic cleavage reaction o a phosphinic acid alkyl ester of the formula IV

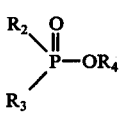

VI wherein $R_2$ and $R_3$ are as defined above and $R_4$ is a member selected from the group consisting of ethyl, isobutyl and 2-ethyl hexyl; wherein the hydrolytic cleavage reaction is carried out in the presence of 2 to 30 weight percent of the phosphinic acid of formula V, based on weight of the corresponding phosphinic acid ester of formula VI, to form the corresponding phosphinic acid and an alkyl alcohol, said process consisting essentially of carrying out the reaction at atmospheric pressure and at a temperature of about 170° to 300° C, while gradually adding during the reaction at least a stoichiometric amount of water sufficient to form said alkyl alcohol and distilling off the alkyl alcohol formed during the reaction.

* * * * *